(12) United States Patent
Roeder et al.

(10) Patent No.: US 9,248,037 B2
(45) Date of Patent: Feb. 2, 2016

(54) AUTOMATIC WIRELESS MEDICAL DEVICE RELEASE MECHANISM

(71) Applicant: Cook Medical Technologies LLC, Bloomington, IN (US)

(72) Inventors: Blayne A. Roeder, Bloomington, IN (US); Zach Wagner, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 340 days.

(21) Appl. No.: 13/838,013

(22) Filed: Mar. 15, 2013

(65) Prior Publication Data

US 2014/0277342 A1  Sep. 18, 2014

(51) Int. Cl.
*A61F 2/966* (2013.01)
*A61F 2/95* (2013.01)

(52) U.S. Cl.
CPC ......... *A61F 2/966* (2013.01); *A61F 2002/9505* (2013.01); *A61F 2002/9511* (2013.01); *A61F 2002/9522* (2013.01); *A61F 2002/9665* (2013.01)

(58) Field of Classification Search
CPC ........... A61F 2/95; A61F 2/962; A61F 2/966; A61F 2002/9505; A61F 2002/9511; A61F 2002/9522; A61F 2002/9665
See application file for complete search history.

(56) References Cited

U.S. PATENT DOCUMENTS

| | | | |
|---|---|---|---|
| 5,242,452 A | 9/1993 | Inoue | |
| 5,295,995 A | 3/1994 | Kleiman | |
| 5,433,706 A | 7/1995 | Abiuso | |
| 5,433,723 A | 7/1995 | Lindenberg et al. | |
| 6,514,282 B1 | 2/2003 | Inoue | |
| 2008/0039925 A1 | 2/2008 | Ishimaru et al. | |
| 2008/0300616 A1* | 12/2008 | Que et al. | 606/191 |
| 2012/0116413 A1 | 5/2012 | Oka et al. | |
| 2013/0253309 A1 | 9/2013 | Allan et al. | |
| 2013/0253342 A1 | 9/2013 | Griswold et al. | |
| 2013/0253343 A1 | 9/2013 | Waldhauser et al. | |
| 2013/0253344 A1 | 9/2013 | Griswold et al. | |
| 2013/0253345 A1 | 9/2013 | Griswold et al. | |
| 2013/0253346 A1 | 9/2013 | Griswold et al. | |
| 2013/0253347 A1 | 9/2013 | Griswold et al. | |
| 2014/0066896 A1 | 3/2014 | Tilson et al. | |

OTHER PUBLICATIONS

Restriction Requirement for U.S. Appl. No. 13/835,877 dated Feb. 3, 2015, 8 pages.
Response to Restriction Requirement for U.S. Appl. No. 13/835,877 dated Apr. 3, 2015, 6 pages.
Office Action for U.S. Appl. No. 13/835,877 dated May 6, 2015, 9 pages.
Response to Office Action for U.S. Appl. No. 13/835,877 dated Aug. 6, 2015, 7 pages.

* cited by examiner

*Primary Examiner* — Ryan Severson
(74) *Attorney, Agent, or Firm* — Brinks Gilson & Lione

(57) ABSTRACT

An automatic wireless medical device release system may reduce the overall diameter of the medical device delivery system. The medical device delivery system may include a medical device with a looped portion at a distal end of the medical device. A capture wire may be located on a delivery tool that is distal to the medical device. The looped portion of the medical device may be attached to a bend in the capture wire. The bend in the capture wire may be maintained by a sheath covering the delivery tool. Removal of the sheath may automatically remove the bend in the capture wire, which may release the looped portion of the medical device from the capture wire.

16 Claims, 3 Drawing Sheets

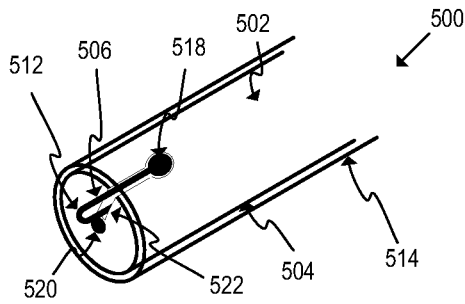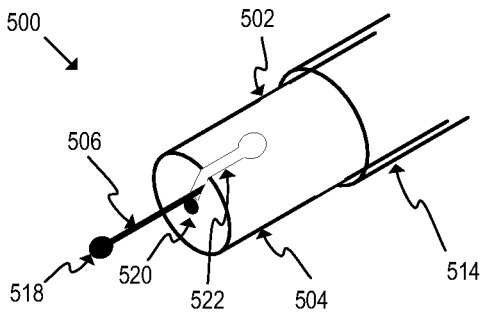
Figure 5A  Figure 5B
FIG. 5
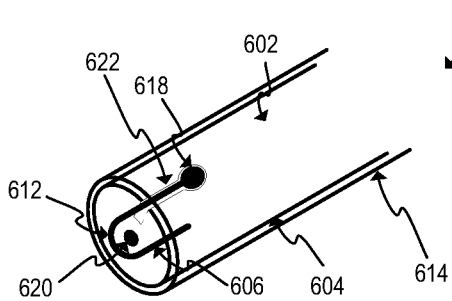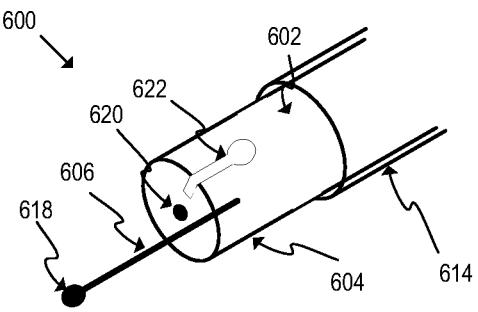
Figure 6A  Figure 6B
FIG. 6
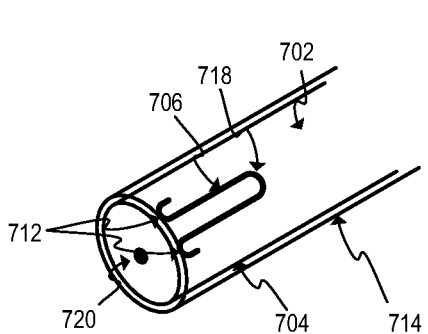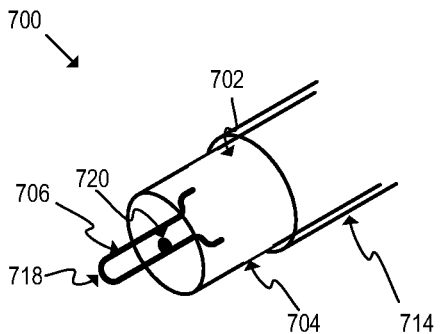
Figure 7A  Figure 7B
FIG. 7

AUTOMATIC WIRELESS MEDICAL DEVICE RELEASE MECHANISM

FIELD OF APPLICATION

This application relates to a medical device delivery system. More particularly, the application relates to a stent-graft delivery system that allows a portion of a self-expanding stent-graft to be released without the use of a trigger wire.

BACKGROUND

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter.

Trigger wires also may be used in conjunction with different stent designs, such as cannula-cut stents having relatively acute or pointed bends. The designs of cannula-cut stents may facilitate compression of the stent to a relatively small delivery profile due to the tight bends of the apices. With such stents, the trigger wires may be looped around one or more vertices formed beneath the proximal and/or distal apices, e.g., a location where an individual apex splits into two separate strut segments.

If trigger wires are threaded through the vertices of such cannula-cut stents, the trigger wires may become crimped at the vertices during compression of the stent to a reduced diameter delivery profile. If the trigger wires are crimped between the strut segments, the trigger wires and/or stent segments may become damaged during delivery, particularly for nickel-titanium stents that may be sensitive to surface imperfections. Furthermore, when compressing a cannula-cut stent having relatively acute bends to a significantly reduced radial profile, barbs disposed near the apices of the stent may become entangled with the stent struts and/or the trigger wires. Still further, in some instance, trigger wires may require a relatively high deployment force when being retracted, and the provision of multiple trigger wires may add to the profile of the delivery system.

SUMMARY OF THE INVENTION

The descriptions below include medical device delivery systems that allow the medical device to be released without the use of trigger wires. In one embodiment, the delivery system includes an expandable medical device having a looped portion extending from a section of the medical device, where the looped portion is resiliently flexible, a shaft comprising a proximal end and a distal end and an interposed internal lumen, the shaft having a capture wire at the proximal end of the shaft, where the capture wire includes a bend to receive the looped portion of the expandable medical device, and a sheath coaxially disposed over the shaft, where the sheath is movable from a first axial position where the sheath covers the capture wire to a second axial position where the capture wire is not covered by the sheath, wherein the expandable medical device is coupled to the shaft when the sheath is in the first axial position.

In another embodiment, a method of releasing an expandable medical device includes delivering an implantable expandable medical device to a desired location, where a looped portion of the medical device surrounds a capture wire located at a proximal end of a shaft and where a sheath is coaxially located over the capture wire, moving the sheath away from the capture wire in a direction parallel to a length of the shaft, uncovering the capture wire, removing the bend from the capture wire, and releasing the looped portion of the implantable expandable medical device from the capture wire.

In another embodiment, the delivery system can be used with an expandable medical device having a resiliently flexible looped portion extending from a section of the expandable medical device, the system includes a shaft comprising a proximal end and a distal end and an interposed internal lumen, the shaft having a capture wire at the proximal end of the shaft, where the capture wire includes a bend to receive the looped portion of the medical device, and a sheath coaxially disposed over the shaft, where the sheath is movable from a first axial position where the sheath covers the capture wire to a second axial position where the capture wire is not covered by the sheath, wherein the expandable medical device is coupled to the shaft when the sheath is in the first axial position.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The accompanying drawings are included to provide a further understanding of the claims, are incorporated in, and constitute a part of this specification. The detailed description and illustrated examples described serve to explain the principles defined by the claims.

FIG. 5 is a perspective view of portions of another exemplary medical device delivery system;

FIG. 6 is a perspective view of portions of another exemplary medical device delivery system;

FIG. 7 is a perspective view of portions of another exemplary medical device delivery system.

DETAILED DESCRIPTION

In the present application, the term "proximal" refers to a direction that is generally closest to the heart during a medical procedure, while the term "distal" refers to a direction that is furthest from the heart during a medical procedure.

Various embodiments of the medical device delivery system are shown in FIGS. 1-8. In general, the medical device delivery system may allow for the release of a portion of a self-expanding medical device from the delivery system without the use of release wires or trigger wires. The medical device may be delivered to a location in a body while the medical device is held in a compressed state by a sheath coaxially located over the medical device. The sheath may radially restrain the medical device. Axial movement of the sheath away from the medical device may allow the medical device to expand. The medical device may include a looped portion that is axially restrained by a capture wire in a delivery tool. The medical device may be releasably attached to delivery tool while the looped portion is restrained by the capture wire. The sheath may cover the capture wire and prevent the looped portion from being removed from the capture wire. The looped portion may be released from the capture wire after the sheath is moved away from the capture wire. The medical device may no longer be attached to the delivery tool after the looped portion is released from the capture wire. The medical device may be fixed in its location in the body after the medical device is no longer attached to the delivery tool.

Figure 1:
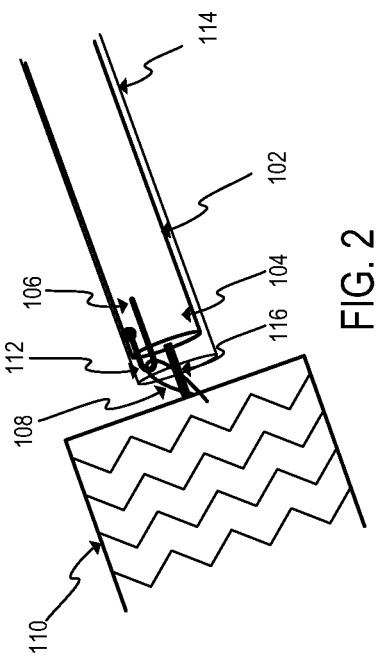
FIG. 1 is a perspective view of an exemplary medical device delivery system.

FIG. 1 is a perspective view of a portion of an exemplary medical device delivery system 100. In FIG. 1, a delivery tool may have a distal end (not shown), a shaft 102, and a proximal end 104. The shaft 102 and proximal end 104 may be cylindrical or any other elongated shape capable of entering a body cavity. The delivery tool may include a lumen provided through the shaft 102. The lumen may allow a guidewire or cannula 116 to pass axially through the delivery tool.

A capture wire 106 may be located at the proximal end 104 of the delivery tool. The capture wire 106 may be any shape capable of allowing a looped portion 108 of a medical device 110 to be held by the capture wire 106. The capture wire 106 may include a bend 112.

Figure 2:
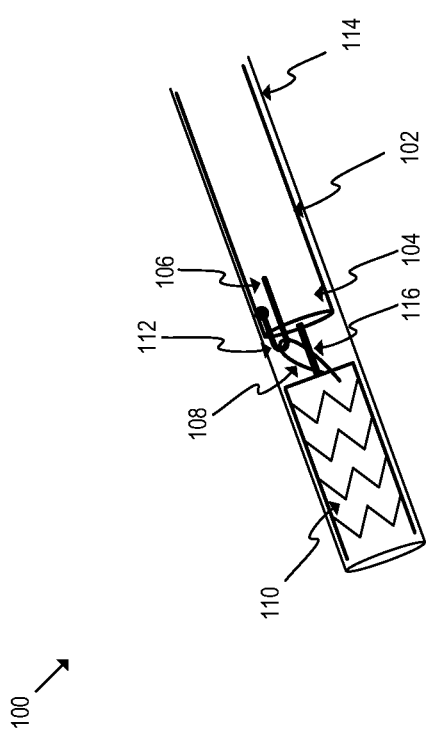
FIG. 2 is a perspective view of the exemplary medical device delivery system.

A medical device 110 may be located proximally from the proximal end 104 of the delivery tool. The medical device 110 may be a stent-graft or any other medical device designed to be located intravascularly or within a body cavity. The medical device 110 shown in FIG. 1 may be shown in compressed state. The medical device may be held in a compressed state by a sheath 114 that is coaxially located over the medical device 110. Sheath 114 may radially restrain the medical device 110 while the sheath 114 is coaxially located over the medical device 110. Removal of sheath 114 may allow medical device 110 to expand radially, as shown in FIG. 2. The medical device may include a looped portion 108 located at its distal end or other section of the medical device. The looped portion 108 may be any resilient and flexible structure, such as a suture, attached to the medical device 110. The looped portion 108 may be tied to the medical device 110 or attached in some other manner such as by rivets or by fusing the looped portion 108 to the medical device 110. The looped portion 108 may be sized to extend around the capture wire 106 while the looped portion 108 is attached to the medical device 110. The looped portion 108 may be sized large enough to allow slight movement of the medical device 110 relative to the delivery tool while the looped portion 108 is located around the capture wire 106.

The medical device delivery system 100 may include a sheath 114 that surrounds the medical device 110, shaft 102, and proximal end 104 of the delivery tool. In FIGS. 1-4, the sheath 114 is shown as transparent to allow objects covered by the sheath 114 to be visible. The sheath 114 may actually be opaque or transparent. The sheath 114 may move axially relative to the shaft 102, as shown in FIGS. 1-4.

FIG. 2 may show the medical device 110 in an expanded state. The compressed or expanded states of medical device 110 shown in FIGS. 1-4 is for illustrative purposes only. The actual amount of compression or expansion may vary as required by the medical device and the application of the medical device delivery system. Movement of sheath 114 axially away from medical device 110, as shown in FIG. 2, may allow medical device 110 to expand.

Figure 3:
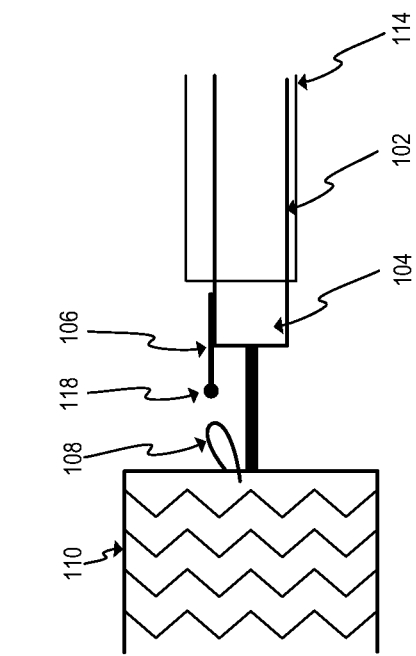
FIG. 3 is a side view of the exemplary medical device delivery system.

FIG. 3 is a side view of the exemplary medical device delivery system 100. In FIG. 3, the looped portion 108 of the expanded medical device 110 may be located around the capture wire 106. Sheath 114 may be located over the capture wire 106. The space shown between the sheath 114 and the delivery tool and capture wire 106 in FIGS. 1-4 may be exaggerated to show the components of the exemplary medical device delivery system 100 more clearly. While the sheath 114 is located over the capture wire 106, the sheath 114 may prevent the bend 112 in the capture wire 106 from straightening. The sheath 114 may restrict the movement of the capture wire 106 while the sheath 114 covers the capture wire 106. The bend 112 in the capture wire 106 may prevent the looped portion 108 of the medical device 110 from releasing or becoming detached from the capture wire 106. The close fit of the sheath 114 over the delivery tool and capture wire 106 may help prevent the looped portion 108 of the medical device 110 from releasing or becoming detached from the capture wire 106.

The capture wire 106 may be shaped to prevent the looped portion 108 of the medical device 110 from releasing or becoming detached from the capture wire 106. The capture wire 106 may be fixed to the proximal end 104 of the delivery tool. Only one section of the capture wire 106 may be fixed to the proximal end 104 of the delivery tool, as shown in FIGS. 1-3. Another section of the capture wire 106 may be free and not attached to the proximal end 104 of the delivery tool.

The free section of the capture wire 106 may include an atraumatic portion 118. The atraumatic portion 118 may prevent damage to a vessel wall or body cavity if the free section of the capture wire 106 contacts vessel wall or body cavity. The atraumatic portion 118 of the free section of the capture wire 106 may take any shape that prevents or minimizes damage to a vessel wall or body cavity that comes in contact with the atraumatic portion 118. The atraumatic portion 118 may consist of, for example, a rounded ball, curved segment, curved end, or cushioned area.

The capture wire 106 may include one or more bends 112 in the free section of the capture wire 106 when the sheath 114 covers the capture wire 106. The capture wire shown in FIGS. 1 and 2 include a single bend 112, however the capture wire 106 may include multiple bends 112. The bend 112 may be a 180 degree bend, as shown in FIGS. 1 and 2, or the angle of the bend may be different depending on the relative locations of the sheath 114, the capture wire 106, and the delivery tool. The capture wire 106 may be held in the bent position by the sheath 114. For example, the free section of capture wire 106 may press against the sheath 114, which may prevent the free section of capture wire 106 from straightening out and removing bend 112. Bend 112 may attach or hook around the looped portion 108 of the medical device 110 and prevent the medical device 110 from moving distally away from the delivery tool.

The capture wire 106 may be composed of any material capable of deforming and later returning to its undeformed shape, such as bending and later straightening. The capture wire 106 may consist of, for example, nitinol or polypropylene filament. The length, thickness, and flexibility of the capture wire 106 may be varied depending on the application. For example, a thicker or less flexible capture wire 106 may be used if the looped portion 108 of the medical device 110 will apply a relatively large force to the capture wire 106. A longer capture wire 106 may be used if the diameter of the looped portion 108 of the medical device 110 is relatively large or if the space between the proximal end 104 of the delivery tool and the sheath 114 is relatively large. The capture wire 106 may return to its undeformed shape automatically. The material properties of capture wire 106 may cause it to return to an unbent or substantially straight shape without any external force applied.

Figure 4:
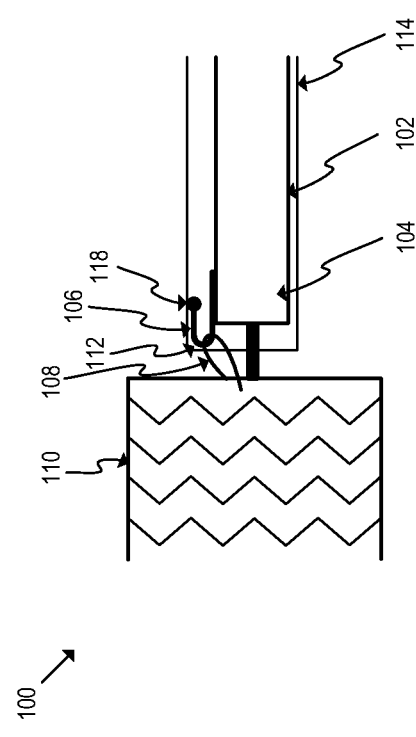
FIG. 4 is another side view of the exemplary medical device delivery system.

FIG. 4 is a side view of the exemplary medical device delivery system 100. In FIG. 4, the sheath 114 has been withdrawn, i.e., moved axially away from the capture wire 106. Moving the sheath 114 away from the capture wire 106 may expose or uncover capture wire 106. After sheath 114 is moved away from capture wire 106 and capture wire 106 is exposed, the bend 112 in capture wire 106 may be removed. Capture wire 106 may remove the bend 112 automatically when the sheath 114 is moved away from capture wire 106. Sheath 114 may have been preventing capture wire 106 from removing the bend 112. The looped portion 108 of the medical device 110 may release or become detached from the capture wire 106 after the sheath 114 is moved away from capture wire 106 and the bend 112 is removed. After looped portion 108 is released from the capture wire 106, the delivery tool may be removed and the previously expanded medical device 110 may remain in place at the desired location.

FIGS. 5-7 are perspective views of portions of other exemplary medical device delivery systems. The exemplary medical device delivery systems in FIGS. 5-7 may include components previous described in reference to exemplary medical device delivery system 100 but not shown in FIGS. 5-7, such as a medical device located proximally from the delivery tool and a guidewire or cannula. The medical device may include a looped portion at the distal end of the medical device, as previously described. In FIGS. 5-7, the sheath may be shown as transparent to allow objects covered by the sheath to be visible. The sheath may actually be opaque or transparent. The space shown between the sheath and the delivery tool in FIGS. 5-7 may be exaggerated to show the components of the exemplary medical device delivery systems more clearly.

In FIG. 5, the exemplary medical device delivery system 500 may include a delivery tool with a distal end (not shown), a shaft 502, and a proximal end 504. The delivery tool may include a lumen 520 provided through the shaft 502. Lumen 520 may extend from the proximal end 504 of the delivery tool to the distal end of the delivery tool. The lumen 520 may allow a guidewire or cannula to pass axially through the delivery tool. A sheath 514 may surround the shaft 502 and proximal end 504 of the delivery tool in exemplary medical device delivery system 500. The sheath 514 may move axially relative to the shaft 502. The inner diameter of the sheath 514 may be similar to the outer diameter of the proximal end 504 of the delivery tool.

Exemplary medical device delivery system 500 may include a capture wire 506 at the proximal end 504 of the delivery tool. The looped portion of the medical device (not shown) may be held in the capture wire 506. The capture wire 506 may be any shape capable of allowing a looped portion of a medical device to surround the capture wire 506. As previously described in reference to exemplary medical device delivery system 100, the capture wire 506 may include a bend 512 and an atraumatic portion 518. The bend 512 may inhibit a looped portion of a medical device from releasing the capture wire 506. The atraumatic portion 518 may prevent damage to a vessel wall or body cavity if the free section of the capture wire 506 contacts vessel wall or body cavity.

Exemplary medical device delivery system 500 may include a recessed area 522. The recessed area 522 may be capable of containing part or all of the free section of capture wire 506, as shown in FIG. 5A. The recessed area 522 may be a similar shape as the free section of capture wire 506, as shown in FIG. 5, or recessed area 522 may be any other shape that is capable of substantially containing the free section of capture wire 506. The recessed area 522 may be larger than the free section of capture wire 506 to allow the free section to easily enter and leave the recessed area 522. The capture wire 506 may be fixed to the proximal end 504 of the delivery tool within recessed area 522, as shown in FIG. 5.

Containing the free section of capture wire 506 within the recessed area 522 may reduce the overall diameter of the delivery tool and capture wire 506. Reducing the overall diameter of the delivery tool and capture wire 506 may minimize the diameter of the sheath 514 covering the delivery tool and capture wire 506. Minimizing the diameter of sheath 514 may make intravascular treatment available to a wider array of patients with more difficult arterial access.

The recessed area 522 may extend to the extreme proximal end 504 of the delivery tool, as shown in FIG. 5, which may allow the capture wire 506 to enter the recessed area 522 from the extreme proximal end 504. Allowing the capture wire 506 to enter the recessed area 522 from the extreme proximal end 504 may prevent any section of capture wire 506 from extending beyond the outer diameter of proximal end 504 while the sheath 514 is covering capture wire 506 and recessed area 522. Preventing the capture wire from extending beyond the outer diameter of proximal end 504 may minimize the diameter of the sheath 514 covering the delivery tool and capture wire 506.

FIG. 5A may show the exemplary medical device delivery system 500 with the sheath 514 covering the capture wire 506 while the capture wire 506 is contained in the recessed area 522. A looped area of a medical device (not shown) could be attached to the bend 512 in the capture wire 506. The sheath 514 may hold the free section of capture wire 506 in the recessed area 522 and prevent the bend 512 from being removed from capture wire 506. In FIG. 5B, the sheath 514 may have been pulled away from capture wire 506, which may uncover the capture wire 506 and recessed area 522. Uncovering the capture wire 506 and recessed area 522 may allow the free section of capture wire 506 to leave the recessed area 522 and may allow capture wire 506 to automatically straighten. A looped area of a medical device may be released from capture wire 506 after it is straightened and bend 512 is removed.

In FIG. 6, exemplary medical device delivery system 600 may include a capture wire 606 attached to the proximal end 604 of the delivery tool. The fixed section of capture wire 606 may be attached to the perimeter of the proximal end 604 of the delivery tool, as shown in FIG. 6. The capture wire 606 may be attached at any location around the perimeter of the proximal end 604. Alternatively, the capture wire 606 may be attached to the extreme proximal end 604 of the delivery tool, such as in a plane that is perpendicular to the longitudinal axis of the delivery tool. Attaching the fixed section of capture wire 606 to the proximal end 604 of the delivery tool at a location outside of the recessed area 622, such as the perimeter of the delivery tool, may allow the bend 612 to have a larger radius of curvature. A large radius of curvature may reduce the strain on capture wire 606 and may improve the durability of capture wire 606.

As discussed in reference to FIGS. 5A and 5B, FIGS. 6A and 6B may show the exemplary medical device delivery system 600 when the sheath 614 may be covering capture wire 606 and recessed area 622 and also when the sheath 614 may have been pulled away from capture wire 606, respectively. Uncovering the capture wire 606 and recessed area 622 may allow the free section of capture wire 606 to leave the recessed area 622 and may allow capture wire 606 to automatically straighten, as shown in FIG. 6B. A looped area of a medical device (not shown) may be released from capture wire 606 after it is straightened and bend 612 is removed. The delivery tool in exemplary medical device 600 may include a lumen 620 provided through the shaft 602. Lumen 620 may extend from the proximal end 604 of the delivery tool to the distal end of the delivery tool. The lumen 620 may allow a guidewire or cannula to pass axially through the delivery tool.

In FIG. 7, exemplary medical device delivery system 700 may include a capture wire 706 attached to the proximal end 704 of the delivery tool. As previously discussed, capture wire 706 may take any shape capable of allowing a looped portion of a medical device (not shown) to be held by the capture wire 706. In FIG. 7, the shape of capture wire 706 may result in two bends 712 when sheath 714 covers capture wire 706. A looped portion of a medical device may surround the free section of capture wire 706 and may contact capture wire 706 at the bends 712. The bends 712 may prevent the looped portion of the medical device from releasing or becoming detached from the capture wire 706 while sheath 714 covers capture wire 706.

The shape of capture wire 706 may also cause the fixed section of capture wire 706 to attach to the perimeter of the proximal end 704 of the delivery tool in more than one place, as shown in FIG. 7. The number of attachment sites of capture wire 706 to the delivery tool may vary and may depend on the material properties of the capture wire 706 or the particular application of the medical device delivery system. In FIG. 7, the atraumatic portion 718 of capture wire 706 may be a curved segment of capture wire 706. As previously discussed, the atraumatic portion 718 may prevent damage to a vessel wall or body cavity if the free section of the capture wire 706 contacts vessel wall or body cavity.

As discussed in reference to FIGS. 5A and 5B, FIGS. 7A and 7B may show the exemplary medical device delivery system 700 when the sheath 714 may be covering capture wire 706 and also when the sheath 714 may have been pulled away from capture wire 606, respectively. Uncovering the capture wire 706 may allow capture wire 706 to automatically straighten, as shown in FIG. 7B. A looped area of a medical device (not shown) may be released from capture wire 706 after it is straightened and bends 712 are removed. The delivery tool in exemplary medical device 700 may include a lumen 720 provided through the shaft 702. Lumen 720 may extend from the proximal end 704 of the delivery tool to the distal end of the delivery tool. The lumen 720 may allow a guidewire or cannula to pass axially through the delivery tool.

Figure 8:
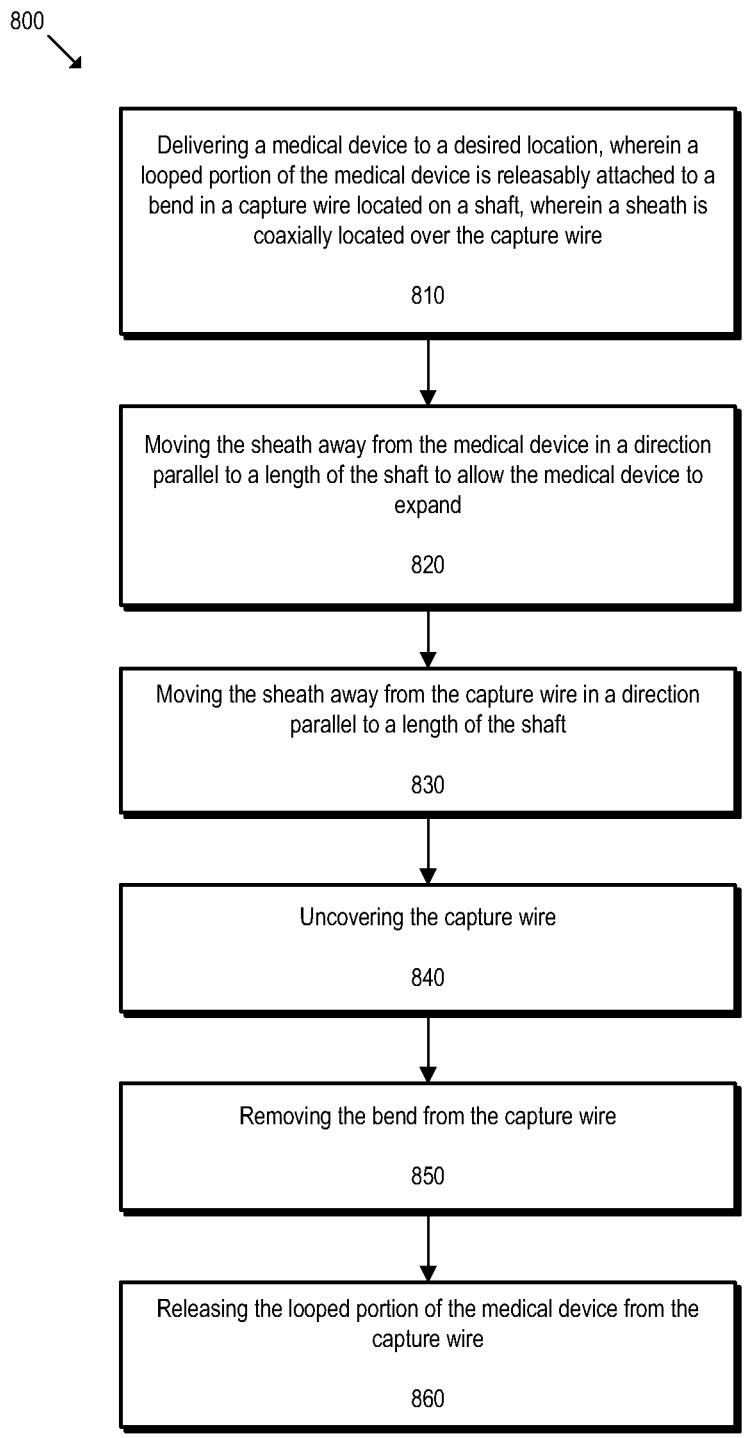
FIG. 8 is a flow diagram of a method for releasing a medical device according to another embodiment of the invention.

FIG. 8 illustrates method 800 for releasing a medical device according to another embodiment of the invention. The method begins with step 810 in which an implantable medical device may be delivered to a desired location. The implantable medical device, such as a stent-graft, may have a looped portion located on its distal end. The looped portion may be releasably attached to a bend in a capture wire, where the capture wire may be located on a shaft of a delivery tool that is distal to the medical device. A sheath may be coaxially located over the capture wire. The sheath may radially restrain the medical device in a compressed state. Step 820 involves moving the sheath away from the medical device in a direction parallel to a length of the shaft to uncover the medical device and allow the medical device to expand. Step 830 involves moving the sheath away from the capture wire in a axial direction that is parallel to the length of the shaft. Step 840 involves uncovering the capture wire by moving the sheath away from the capture wire. Step 850 involves removing the bend from the capture wire. Step 860 involves releasing the looped portion of the medical device from the capture wire, which may release the medical device from the delivery tool.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A medical device delivery system comprising:
an expandable medical device having a looped portion extending from a section of the medical device, wherein the looped portion is resiliently flexible;
a shaft comprising a proximal end and a distal end and an interposed internal lumen, the shaft having a capture wire at the proximal end of the shaft, wherein the capture wire includes a bend to receive the looped portion of the expandable medical device and has a free section that is not attached to the shaft;
a sheath coaxially disposed over the shaft, wherein the sheath is movable from a first axial position where the sheath covers the capture wire to a second axial position where the capture wire is not covered by the sheath, wherein the expandable medical device is coupled to the shaft when the sheath is in the first axial position, and wherein the shaft further comprises a recess in the shaft that is sized and configured to contain the entire end of the free section within the recess.

2. The system of claim 1, wherein the free section of the capture wire has an atraumatic portion comprising an enlarged portion at the end of the free section, and wherein the recess has a shape conforming to the shape of the end of the free section .

3. The system of claim 1, wherein the capture wire is attached to the shaft at the recess.

4. The system of claim 1, wherein an outer diameter of the shaft at the capture wire is the same as an inner diameter of the sheath.

5. The system of claim 1, wherein the sheath maintains the capture wire free end within the recess when the sheath is in the first axial position.

6. The system of claim 1, wherein the bend in the capture wire is maintained while the sheath is in the first axial position.

7. The system of claim 1, wherein the bend in the capture wire is automatically removed when the sheath is in the second axial position.

8. The system of claim 1, wherein the bend in the capture wire comprises a 180 degree bend.

9. The system of claim 1, wherein the medical device is a stent graft.

10. The system of claim 9, wherein the looped portion comprises a suture attached to the stent graft.

11. A method of releasing an expandable medical device, comprising:
- delivering an implantable expandable medical device to a desired location, wherein a looped portion of the medical device engages a bend in a capture wire located at a proximal end of a shaft, wherein a sheath is coaxially disposed over the capture wire, the capture wire having a free section that is unattached to the shaft having a length and shape, and the shaft having a recess within the shaft having a length and a shape that conforms to the free section length and shape and within which the free section is entirely disposed;
- moving the sheath away from the capture wire in a direction parallel to a length of the shaft;
- uncovering the capture wire;
- removing the bend from the capture wire; and
- releasing the looped portion of the implantable expandable medical device from the capture wire.

12. The method of claim 11, wherein the bend in the capture wire is automatically removed when the sheath uncovers the capture wire.

13. A medical device delivery system for use with an expandable medical device having a looped portion extending from a section of the expandable medical device, the system comprising:
- a shaft comprising a proximal end and a distal end and an interposed internal lumen, the shaft having a capture wire at the proximal end of the shaft, and a recess within the shaft, and wherein the capture wire includes a bend to receive the looped portion of the medical device and a free section that is unattached to the shaft, wherein the free section is disposed entirely within the recess; and
- a sheath coaxially disposed over the shaft, wherein the sheath is movable from a first axial position where the sheath covers the capture wire to a second axial position where the capture wire is not covered by the sheath, wherein the expandable medical device is coupled to the shaft when the sheath is in the first axial position.

14. The system of claim 13, wherein an outer diameter of the shaft at the capture wire is the same as an inner diameter of the sheath.

15. The system of claim 13, wherein the bend in the capture wire is maintained while the sheath is in the first axial position.

16. The system of claim 13, wherein the bend in the capture wire is automatically removed when the sheath is in the second axial position.

* * * * *